US008118431B2

(12) United States Patent
Shea et al.

(10) Patent No.: US 8,118,431 B2
(45) Date of Patent: Feb. 21, 2012

(54) SPLIT VIEW ADAPTER FOR A MICROSCOPE

(75) Inventors: William Shea, Pleasanton, CA (US);
Phillip Baker, Walnut Grove, CA (US);
Barry Linder, Danville, CA (US)

(73) Assignee: Clarity Medical Systems, Inc.,
Pleasanton, CA (US)

(*) Notice: Subject to any disclaimer, the term of this patent is extended or adjusted under 35 U.S.C. 154(b) by 87 days.

(21) Appl. No.: 12/606,982

(22) Filed: Oct. 27, 2009

(65) Prior Publication Data

US 2010/0118269 A1    May 13, 2010

Related U.S. Application Data

(60) Provisional application No. 61/111,980, filed on Nov. 6, 2008.

(51) Int. Cl.
*A61B 3/00* (2006.01)
*G02C 7/04* (2006.01)

(52) U.S. Cl. .................................. 351/219; 351/160 R
(58) Field of Classification Search .................. 359/368, 359/381, 385, 388, 389; 351/160 R, 205, 351/206, 211, 212, 214, 219, 221; 396/51
See application file for complete search history.

(56) References Cited

U.S. PATENT DOCUMENTS 2,168,637 A * 8/1939 Whitwell ...................... 359/737
6,142,630 A * 11/2000 Koester ......................... 351/219

* cited by examiner

*Primary Examiner* — Ricky Mack
*Assistant Examiner* — Mahidere Sahle
(74) *Attorney, Agent, or Firm* — Charles E. Krueger

(57) ABSTRACT

This invention discloses an apparatus that is attached to the objective lens of a microscope to split its field of view into at least two. In one embodiment, a mirrored gonio lens is snapped to the objective of an ophthalmic surgical microscope to provide a view of the eye's anterior surface and a view of the eye's anterior chamber.

7 Claims, 1 Drawing Sheet

SPLIT VIEW ADAPTER FOR A MICROSCOPE

RELATED APPLICATIONS

This application claims priority from a provisional application entitled SLIT VIEW ADAPTER FOR A MICROSCOPE, Application No. 61/111,980, filed Nov. 6, 2008, which is hereby incorporated by reference for all purposes.

TECHNICAL FIELD

The present disclosure relates generally to surgical microscopes for eye imaging and operation.

DESCRIPTION OF EXAMPLE EMBODIMENTS

Overview

Figure 1:
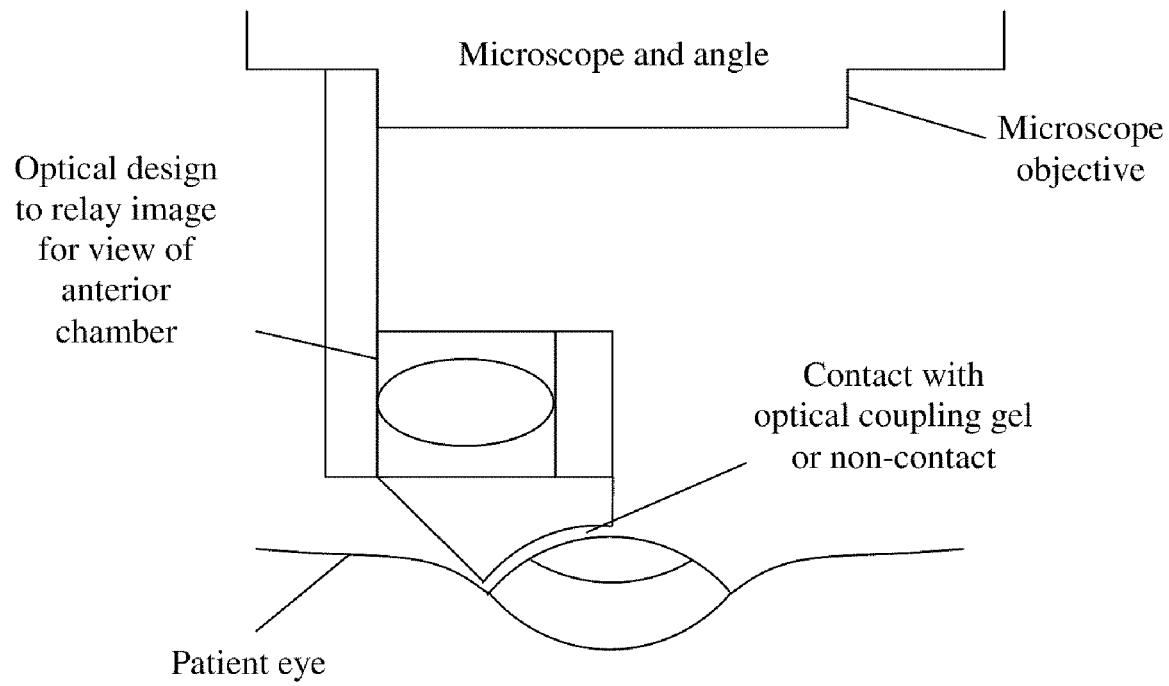
FIG. 1 illustrates the presently invented adaptor attached to a surgical microscope for eye surgical operation and FIG. 2 illustrates the mirror/prism and the lens included in the adaptor.
Figure 2:
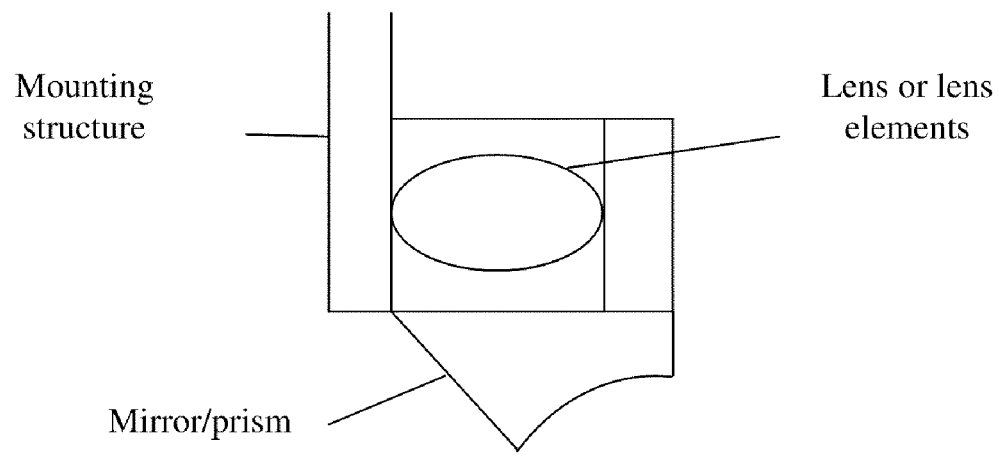

An example embodiment is an apparatus that can adapt itself to the objective lens of a microscope thus enabling the microscope to present a split view of at least two. In one embodiment, a mirrored gonio lens specially adapted to the imaging of the anterior chamber structures is mounted on a mechanical adaptor that snaps to the objective of an ophthalmic surgical microscope and as a result, it provides a view of the eye's anterior surface and a view of the eye's anterior chamber. The field of view as seen through the microscope is now a "split view" adaptation to the microscope.

Description

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

Traditional surgical microscopes only provide a common field of view for the entire object being examined. However, in certain eye surgical operations such as those for closed angle glaucoma, it is desirable to have not only a live view of the front of the eye (cornea and orbit) but also a live view of the inside of the anterior chamber. This challenge has not been addressed yet.

In an example embodiment, an apparatus and method is disclosed that can adapt an optical element to the objective lens of a microscope to split the field of view into at least two, of which half the field can be used for the visualization of one portion of the object and the remaining half can be used to visualize a second portion of the object. For example, in closed angle glaucoma screening or surgical operation, a view of the eye's anterior surface (external view of cornea and orbit) and a view of the eye's anterior chamber (includes iris, anterior lens capsule, pupil, and angle with a clear and accurate view of the anatomical structures including scleral spur, pigment, trabecular meshwork, ciliary body and Schwabe's Line, etc.) can be displayed live on the same monitor. The visualization of the anterior chamber can be achieved through an optical design that relays the anterior chamber image to be conjugate with the anterior image. The optical design can be either contact or non-contact with the eye. The optical design can include a prism/mirror element and other lens elements to provide the desired effect.

The apparatus can be a one-time use device that is sold as a sterile product to the end user, or the part of the apparatus that comes in contact with the patient can be the sterile disposable component. In either case, the design intent is to make it easy to attach and remove the device from a surgical microscope by adapting to the objective lens in a variety of ways such as mounting directly on its standard threads. The adaptor that mounts the optical relay component(s) can also provide articulation in the x, y, or z axis to facilitate positioning to the eye or for moving the device out of the field of view without having to disconnect it from the microscope. The adaptation can also be designed to maintain a close working distance relationship between the object distance of the main objective lens and the object distance of the second adapted combined objective lens. This will offer the viewer the ability to rapidly switch between anterior field of view and anterior chamber field of view. The apparatus can also include the use of lenticular optics to provide better image definition and/or a polarization enhancement of the "Split View".

The presently described example embodiments can be applied to different kinds of eye surgeries to provide better visualization inside-and-out of the eye during the surgery. For example, for glaucoma surgery, such a split view visualization is important during trabeculectomy or any ab-interno procedure such as a stent, shunt, or any drainage device implant, or laser trabecular procedure such as excimer (ELT), or any other surgery involving the angle structures such as needling of an internal ostium.

The presently described apparatus and method will provide the ophthalmologist/surgeon the ability to visualize the mechanics of surgery of making an incision and placement of tools through the cornea into the anterior chamber while at the same time visualize the placement of an IOL and its haptics, shunt, or other device in the anterior chamber to ensure correct/optimal placement. This solves the current inability of the surgeon to accurately/precisely see in real-time the placement of the device at the same time. In doing so, the need to possibly go back and correct for poor device placement would be reduced. It also provides the surgeon the real-time ability to confirm accurate placement and functionality intra-operatively.

It should be noted that this example embodiment can also provide two or more levels of visual magnification. The optical element that is adapted to the microscope objective lens can comprise a number of lenses which can be individually switched into the optical path, or as an alternative any number of these lenses can be stacked and inserted into the optical path to provide different optical magnifications. For example, with this example embodiment the anterior image could be magnified 2× in half of the FOV while the other is at the microscope's magnification.

In addition to eye surgeries, the present invention can also be extended to any other intra-operative surgeries requiring visualization through a microscope, whether or not they are related to the eye, including applications that utilize magnification modalities such as wafer inspection, microbiology, machine inspection.

The invention has now been described with reference to the example embodiments. Alternatives and substitutions will now be apparent to persons of skill in the art. Accordingly, it is not intended to limit the invention except as provided by the appended claims.

What is claimed is:

1. An apparatus configured to be attached to a microscope, with the microscope including an objective lens and configured to have a common field of view of an image of the anterior surface of a subject eye, said apparatus comprising:
   an optical relay component including a beam redirecting element and a lens element; and
   an adaptor configured to be connected to the surgical microscope and to mount the optical relay component, with the adaptor configured to place the optical relay component between the subject eye and the objective lens to split the field of view of the microscope, with the optical relay component configured to image the anterior chamber of the eye and to relay an image of the anterior chamber to the objective lens that is conjugate to the view of the anterior surface of the subject eye so that the microscope has a split field of view of the anterior surface and of the anterior chamber of the subject eye.

2. The apparatus of claim 1, wherein the optical relay component includes a mirrored gonio lens specially adapted to the imaging of the anterior chamber structures.

3. The apparatus of claim 1 wherein the adaptor snaps to the objective of an ophthalmic surgical microscope.

4. The apparatus of claim 1 where the beam redirecting element is a minor.

5. The apparatus of claim 1 where the beam redirecting element is a prism.

6. The apparatus of claim 1 where the adaptor is configured to articulate so that the position of the optical relay component relative to the subject eye and the objective lens can be varied.

7. The apparatus of claim 1 where the microscope includes standard threads into which the objective lens is threaded and where the adaptor is mounted directly on the standard threads.

* * * * *